United States Patent [19]

Ogawa et al.

[11] Patent Number: 4,699,705

[45] Date of Patent: Oct. 13, 1987

[54] ELEMENT FOR ELECTROPHORESIS USING AQUEOUS POLYACRYLAMIDE GEL

[75] Inventors: Masashi Ogawa, Asaka; Hiroyuki Tamaki, Fujinomiya, both of Japan

[73] Assignee: Director of The Finance Division Minister's Secretariat Science and Technology Agency, Tokyo, Japan

[21] Appl. No.: 854,345

[22] Filed: Apr. 21, 1986

Related U.S. Application Data

[63] Continuation of Ser. No. 612,608, May 21, 1984, abandoned.

[30] Foreign Application Priority Data

May 19, 1983 [JP] Japan .................................. 58-87965

[51] Int. Cl.$^4$ ............................................. B01D 13/00
[52] U.S. Cl. ............................... 204/299 R; 204/182.8
[58] Field of Search .................... 204/299 R, 182.8; 427/40; 428/500

[56] References Cited

U.S. PATENT DOCUMENTS

| | | | |
|---|---|---|---|
| 4,415,428 | 11/1983 | Nochumson et al. | 204/299 R |
| 4,481,094 | 11/1984 | Fernandez de Castro et al. | 204/299 R X |
| 4,548,869 | 10/1985 | Ogawa et al. | 204/299 R |
| 4,548,870 | 10/1985 | Ogawa et al. | 204/182.8 |
| 4,579,783 | 4/1986 | Ogawa et al. | 204/182.8 X |
| 4,600,641 | 7/1986 | Ogawa et al. | 204/299 R |

*Primary Examiner*—John F. Niebling
*Assistant Examiner*—John S. Starsiak, Jr.
*Attorney, Agent, or Firm*—Jules E. Goldberg

[57] ABSTRACT

An element for electrophoresis comprising a polymer sheet having been subjected to glow discharge treatment and an aqueous gel medium layer containing a compound having at least one carbamoyl group (modifier, e.g., urea and formamide) and being provided on the sheet. The aqueous gel medium layer preferably comprises an aqueous polyacrylamide gel formed by crosslinking polymerization of an acrylamide compound and a crosslinking agent in the presence of water.

Further, the medium layer preferably contains a water-soluble polymer and agarose.

10 Claims, No Drawings

ELEMENT FOR ELECTROPHORESIS USING AQUEOUS POLYACRYLAMIDE GEL

This is a continuation of application Ser. No. 612,608, filed May 21, 1984, now abandoned.

BACKGROUND OF OF THE INVENTION

1. Field of the invention

This invention relates to an element for electrophoresis, and more particularly relates to an element for electrophoresis suitably employable for determination of base sequence of DNA, RNA, their fragments, and their derivatives.

2. Description of prior arts

In the method for determination of the base sequence of DNA, RNA, their fragments, and their derivatives according to the post-label method, the operation of slab electrophoresis using a polyacrylamide gel membrane has become essential. Since the study in the genetic engineering technology has advanced recently, quick determination of the base sequence of DNA, etc. is highly desired.

The polyacrylamide gel membrane employable for the above purpose can be prepared by crosslinking polymerization of a monomer such as acrylamide and a two-functional crosslinking agent such as N,N'-methylenebisacrylamide under an oxygen-free condition in the presence of water and a polymerization catalyst. In the course of the preparation of the polyacrylamide gel membrane, a modifier such as urea or formamide is generally incorporated into the membrane.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3–1 mm); sealing the gel-forming soluton from oxygen; and causing the crosslinking polymerization to prepare the desired gel membrane. The procedure employing the glass plates are disadvantageous because the glass plate is easily breakable and rather heavy, and careful handling is accordingly required. Thus, the above procedure employing the glass plates is difficultly utilized to prepare the polyacrylamide gel membranes in a mass scale.

The polyacrylamide gel member prepared as above is employed for electrophoresis in the manner such as described below.

The polyacrylamide gel membrane is vertically placed in the form of being sandwiched between the glass plates, and in the first place a pre-electrophoresis operation is carried out. Then, a certain amount of a sample (=P-labeled DNA cleaved by Maxam-Gilbert method) is introduced into sample slots provided on the membrane, and electrophoresis is carried out. After the electrophoresis is carried out for a certain period of time (e.g., approx. 6-12 hours), one glass plate is removed carefully the exposed gel membrane is covered with a polymer film such as poly(vinylidene chloride) for being subjected to autoradiographic process. The autoradiographic process is carried out by the following procedures: A radiographic film and an intensifying screen are superposed successively on the film covering the gel membrane, whereby exposing the radiographic film to the gel membrane at a low temperature (e.g., −80° C.) for a certain period of time (e.g., approx. 10-20 hours). After the exposing procedure, the radiographic film is developed, and the resolved pattern reproduced on the film is studied for determination of the base sequence of DNA, etc.

Since the autoradiographic process requires a long period as described above, it has been desired that the operation period is shortened. Moreover, enhancement of resolution accuracy in the detection of the resolved pattern is desired.

It is known that the resolution accuracy can be enhanced by applying the autoradiographic process to the gel membrane in dry state. The procedure for drying the gel membrane can be carried out as follows. The gel membrane having been subjected to electrophoresis is immersed in 10% aqueous acetic acid solution so as to fix the resolved DNA cleavage products as well as to remove the modifier such as urea from the membrane. The adhesion between the glass plate and tne gel membrane is weak or negligible, the gel membrane easily separates from the glass plate and floats in the solution. The separated gel membrane is carefully taken out, placed on a filter paper, and dried under reduced pressure. The membrane is thus dried and fixed onto the filter paper. The autoradiographic process applied to the dry membrane shows highly enhanced resolution. However, the drying process has such drawbacks that the separation and drying stages require highly trained skill and careful handling and actually the membrane is sometimes broken in these stages.

SUMMARY OF THE INVENTION

An object of the present invention is to provide an element for electrophoresis which is improved in the adhesion between the support and the aqeuous gel medium such as in the form of a membrane under wet condition.

Another object of the present invention is to provide a element for electrophoresis which is substantially free from sepration between the polyacrylamide gel medium and the support in the course of a stage for removing modifier (e.g., urea) and a subsequent drying stage.

There is provided by the present invention an element for electrophoresis comprising a polymer sheet having been subjected to glow discharge treatment and an aqueous gel medium layer containing a compound having at least one carbamoyl group and being provided on the sheet.

The element for electrophoresis of the present invention comprises a two-layer structure in which the support layer and the medium layer are combined directly through the hydrophilically treated surface of the support. This two-layer structure hardly separates in the course of a variety of operations performed in the aforementioned drying stage. Accordingly, the medium (or membrane) is hardly broken in the handling. Further, no filter paper is needed in the autoradiographic process.

Moreover, the element for electrophoresis of the present invention can be prepared by forming the medium layer directly on the sheet. Therefore, the element for electrophoresis of the invention is advantageously prepared in a mass scale.

DETAILED DESCRIPTION OF THE INVENTION

Examples of the support employable for the preparation of the element for electrophoresis of the present invention include a variety of polymer materials in the form of sheet (the term "sheet" includes a film and a plate). Examples of the polymer materials include polyethylene terephthalate, polycarbonate of Bisphenol A, polyvinyl chloride, vinylidene chloride-vinyl chloride copolymer, polymethyl methacrylate, polyethylene, polypropylene, cellulose acetates, and cellulose acetate propionate. Preferred is a polyethylene terephthalate sheet.

The support employed in the present invention is subjected to glow discharge treatment prior to the provision of the aqueous gel medium layer thereon.

The glow discharge treatment is applied onto the support under such conditions that the surface of the support can be made hydrophilic. The glow discharge treatment for making a surface of a polymer material hydrophilic is already known. Accordingly, such known arts can be applied for the glow discharge treatment of the support of the element of the invention. For example, the glow discharge treatment can be carried out by causing glow discharge on a surface of a support material moving under vacuum containing oxygen at a partial pressure of lower than 1 Torr. The art of glow discharge treatment for a plastic material is disclosed in Japanese Patent Provisional Publications No. 55(1980)-18469, No. 53(1978)-129262, No. 51(1976)-54672, etc. The conditions of the glow discharge treatment disclosed in these publications can be applied to the glow discharge treatment for the support of the element of the present invention.

The glow discharge treatment for the support is generally applied to the surface for receiving an aqueous gel medium. But, the glow discharge treatment can be also applied to another surface of the support. If the glow discharge treatment is applied also to the reverse side, said side can be advantageously combined with a glass plate with water but without an adhesive in the case that the element for electrophoresis of the invention is to be tentatively arranged on a glass plate.

The aqueous gel medium layer is now described in more detail.

Examples of the aqueous gel medium (may be referred to herein as "gel membrane") employed in the present invention include a medium layer for electrophoresis consisting essentially of an aqueous polyacrylamide gel formed by crosslinking polymerization of an acrylamide compound and a crosslinking agent in the presence of water.

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the acrylamide compound employable in the present invention include acryamide and its homologues such as N-methylacrylamide, N,N-dimethylacrylamide, amide, N-(hydroxymethyl)acrylamide and diacetonacrylamide, and these compounds may be employed independently or in combination. Acrylamide is most preferable among these acrylamide compounds, and said acrylamide can be also preferably employed in combination with one or more of other acrylamide compounds.

As the crosslinking agent employable to obtain the polyacrylamide gel membrane of the invention, a known crosslinking agent described, for instance, in "Electrophoresis" 1981, 2, 213–228 can be employed singly or in combination. Examples of the crosslinking agent include bifunctional compounds such as N,N'-methylenebisacrylamide (BIS), N N'-propylenebisacrylamide (PBA), diacrylamide dimethylether (N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD), and N,N'-bisacrylylcystamine (BAC). The crosslinking agent can be employed in the amount of approx. 2 to 30 wt. %, preferably approx. 3 to 10 wt. %, based on the total weight of the monomer (i.e., acrylamide compound) and the crosslinking agent. The gel concentration preferably is in the range of approx. 3 to 30 wt/v % (total weight of monomer and crosslinking agent per total volume ,of gel membrane comprising monomer, crosslinking agent and aqueous medium), the concentration being in accordance with the diffinition indicated by S. Hjerten in "Arch. Biochem. Biophys." 1 (Suppl.), 147 (1962).

As the modifier, a compound containing at least one carbamoyl group is employed. Examples of the modifier include urea and formamide. Urea is most preferred. The modifier can be used in an amount of approx. 40 to 60 wt. % based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

A pH buffer agent can be contained in the aqueous gel membrane of the invention. Any buffer agent which is able to buffer a solution to a range of pH 8.0 to 9.0. preferably pH 8.2 to 8.3 can be used. Buffer agents employable in the invention are described in publications such as "Chemistry Handbook, Fundamental Edition" compiled by The Chemical Society of Japan (Maruzen Ltd., Tokyo, 1966) pages 1312–1320; "Modern Electrophoresis" editted by Aoki & Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include tris(hydroxymethyl)aminomethane (Tris), N,N-bis(2hydroxyethyl)glycine (Bicine), N-2hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl]-3-aminopropanesulfonic acid (TAPS) or its Na or K salt; as well as an acid, an alkali, and a salt employable in combination with these compounds. Preferable examples of the buffer agent include Tris, boric acid-EDTA.2Na (pH 8.3).

The aqueous gel membrane of the invention preferably contains a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of the polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in a range of approx. 2 to 100 wt. %, preferably, approx. 5 to 50 wt. %, based on the total weight of the monomer and crosslinking agent.

The addition of a water-soluble polymer serves to impart elasticity to the gel membrane, and thus modified gel membrane is still elastic even if it is dried. Thus, the gel membrane is so improved as to be free from the brittleness, whereby the gel membrane becomes hardly breakable. Further, the viscosity of the gel membrane can be controlled by selecting the molecular weight and amount of the water-soluble polymer.

The aqueous gel membrane preferably contains agarose. There is no specific limitation on the agarose to be contained in the gel membrane, and any type of agarose such as low-electroendosmosis agarose, medium-electroendomosis agarose, or high-electroendomosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB 2 042 571A), 57(1982)-502098 (WO No. 82/02599, U.S. Pat. No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel-forming solution can be controlled through changing the temperature of the solution, whereby suppressing flowability of the solution as well as facilitating the formation of the gel membrane.

The aqeous gel membrane of the element of the invention can be formed by radical crosslinking polymerization between a monomer such as acrylamide with the bifunctional compound (crosslinking agent) in an aqueous medium in which the water-soluble polymer and agarose are dissolved almost homogeneously. The gel is assumed to have a structure in which the water-soluble polymer and agarose are dispersed in the three-dimensionally crosslinked polymer formed by the reaction of the monomer and cross-linking agent, and the water-soluble polymer and agarose are dispersed and are further entangle with the three-dimensionally crosslinked polymer structure.

The crosslinking polymerization can be initiated by a known method, for instance, in the presence of a peroxide and/or under irradiation of ultra-violet rays. The reaction can be further accelerated by heat and irradiation with ultra-violet rays.

As the polymerization catalyst, a known low temperature-polymerization initiator such as those described in "Electrophoresis" 1981, 2, 213–219, ibid. 1981, 2, 220–228; and "Modern Electrophoresis" editted by Aoki & Nagai (Hirokawa Shoten, 1973) can be used. Examples of the initiator include a mixture of $\beta$-dimethylaminopropionitrile (DMAP) and ammonium peroxodisulfate, a mixture of N,N,N',N'-tetramethylenediamine (TEMED) and ammonium peroxodisulfate, a mixture of TEMED and riboflavin, a combination of a mixture of TEMED, riboflavin and hydrogen peroxide, and irradiation with ultra-violet rays. The radical reaction initiator can be employed in the amount of approx. 0.3 to 5 wt. %, preferably approx. 0.5 to 3 wt. %, based on the total amount of the monomer and crosslinking agent.

The aqueous gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

A polyol compound such as glycerol or ethylene glycol can be contained in the aqueous gel membrane of the element of the invention as a wetting agent. The polyol compound can be introduced in an amount of approx. 5 to 40 wt. % based on the volume of the aqueous gel membrane. Glycerol is particularly preferable among the polyol compounds. The addition of the wetting agent serves to keep the gel membrane from exdessive dryness possibly caused by evaporation of water during storage of the medium, whereby preventing the medium from turning brittle or cracking caused by the excessive dryness. Thus, the improvement of physical properties of the gel membrane is accomplished.

The gel membrane of the element of the invention can be prepared by a process in which a gel forming solution is coated by a known method on an electric insulation support having a hydrophilic surface, the surface of which has been given by the aforementioned glow discharge treatment. The gel forming solution is then crosslinked to polymerization on the surface of the support.

In the case the gel forming solution is crosslinked on the surface of the support, the surface of the gel forming solution layer can be covered with a covering material such as a film, sheet, or plate. The same material as employable for the support can be employed as the covering material. The covering material may be previously so treated by glow discharge treatment to have a hydrophilic surface. The covering material has thickness of not more than 200 $\mu$m, and preferably has approx. 4–200 $\mu$m, from the practical viewpoint.

In the case that the covering material is thick (e.g., approx. 70–300 $\mu$m), the element of the present invention can be prepared by the following steps: the gel forming solution is first coated on the covering material and crosslinked thereon to form the desired gel medium layer, and then a support having the hydrophilic surface is provided on the gel medium layer.

The gel membrane of the invention can be employed for the horizontal or vertical electrophoresis, disc electrophoresis, etc. by known methods described, for instance, in the aforementioned texts.

The medium for electrophoresis provided to the element of the present invention is strongly bound to the support through the hydrophilically treated surface of the support. Accordingly, the element for electrophoresis of the present invention is always kept in the form of an integrated unit in the course of ordinary operations. For this reason, the complicated operations conventionally required in the electrophoresis for determination of base sequence of DNA, etc. can be simplified by the use of the element for electrophoresis according to the present invention. Moreover, the electrophoresis operation and drying operation can be performed by the integrated structure comprising the support and the gel membrane provided thereon.

The present invention will be more clearly understood with reference to the following examples.

EXAMPLE 1

A transparent polyethylene terephthalate (PET) sheet (thickness 180 μm) with no color was moved at a rate of 10 m/min. under vacuum (oxygen pressure: 0.05 Torr) and simultaneously subjected to glow discharge treatment (200 V, 1.0 A) on the surface. Thus, a support having a hydrophilic surface was prepared.

On the surface of the support having been treated to the glow discharge treatment was formed a polyacrylamide gel membrane of 0.5 mm thick by coating an aqueous solution containing 11.87 g. of acrylamide, 0.63 g. of BIS, 42 g of urea, 1.08 g. of tris(hydroxymethyl)aminomethane [CAS Registry No. 77-86-1], 0.55 g. of boric acid, and 93 mg of EDTA Na salt 100 ml. volume after addition of 1.3 ml of ammonium peroxodisulfate (5 weight %) and 33 μl. of TEMED, both being the polymerization initiators. Thus, an element for electrophoresis was obtained.

For comparison, another element for electrophoresis was prepared using the PET support not having been subjected to glow discharge treatment.

The adhesiveness between the polyacrylamide gel membrane and the support in the element for electrophoresis was evaluated by pressing the gel membrane. As a result, it was observed that the element using the support having been subjected to the glow discharge treatment was satisfactory in the adhesiveness and the gel membrane thereof was strongly fixed onto the support, while the element using the untreated support was poor in the adhesiveness, and the gel membrane easily separated.

EXAMPLE 2

The PET sheet was subjected to the glow discharge treatment under the same conditions as in Example 1, to make the surface hydrophilic. On the treated surface of the support was formed a polyacrylamide gel membrane of 0.5 mm thick by coating an aqueous solution containing 11.87 g. of acrylamide, 0.63 g. of BIS, 0.3 g. of agarose (low electroendosmosis, gelation temperature 36° C.), 2.5 g. of polyacrylamide, 42 g. of urea, 1.08 g. of tris(hydroxymethyl)aminomethane, 0.55 g. of boric acid, and 93 mg. of EDTA Na salt in 100 ml. volume after addition of 1.3 ml of ammonium peroxodisulfate (5 weight %) and 33 μl. of TEMED, both being the polymerization initiator. Thus, an element for electrophoresis was obtained.

For comparison, another element for electrophoresis was prepared using the PET support not having been subjected to glow discharge treatment.

A sample ($^{32}$P-DNA cleaved by Maxam-Gilbert method) was electrophoresed on the polyacrylamide gel membrane for sequencing the DNA. The element was then immersed in 10% aqueous acetic acid solution for 1 hour so as to remove the urea and fix the resolved substance to the membrane. In this immersing stage, the adhesiveness between the support and the polyacrylamide gel membrane was observed for each element.

In the element using the support having been subjected to the glow discharge treatment, the gel membrane was were completely bound to the support during the immersing and drying process. In addition, no unsatisfactory results were observed in the autoradiographic process in the use of said element.

In contrast, in the the element using the support not having been subjected to glow discharge treatment (control sample), the gel membrane separated rather easily from the support immediately after the element was immersed in the solution.

We claim:

1. An element for electrophoresis comprising:
   a polymer sheet having been subjected to glow discharge treatment; and
   an aqueous polyacrylamide gel medium layer which is provided on the polymer sheet and contains a water-soluble polymer selected from the group consisting of polyacrylamide and polyethylene glycol, agarose and a compound selected from the group consisting of urea and formamide, the aqueous polyacrylamide gel medium layer being formed by crosslinking polymerization of an acrylamide compound and a crosslinking agent in the presence of water.

2. The element for electrophoresis as claimed in claim 1, in which said polymer sheet is a polyethylene terephthalate sheet.

3. The element for electrophoresis as claimed in claim 1 in which a polymer sheet having been subjected to glow discharge treatment is provided on said aqueous gel medium layer thereby sandwiching the medium layer between the two polymer sheets.

4. The element for electrophoresis as claimed in claim 1 in which said water-soluble polymer is contained in the amount of 2 to 100 wt. % based on the polyacrylamide solid amount and said agarose is contained in the aqueous polyacrylamide gel medium in the amount of 0.2 to 2 wt/v %.

5. The element for electrophoresis as claimed in claim 4 in which said polymer sheet is a polyethylene terephthalate sheet.

6. The element for electrophoresis as claimed in claim 4 in which a polymer sheet having been subjected to glow discharge treatment is provided on said aqueous gel medium layer thereby sandwiching the medium layer between the two polymer sheets.

7. The element for electrophoresis as claimed in claim 1 in which the water soluble polymer and agarose are dispersed in a three-dimensionally crosslinked polymer formed by the polymerization reaction of the acrylamide compound and the crosslinking agent and are entangled with the three-dimensionally crosslinked polymer structure.

8. In a method for determination of base sequence of a sample selected from the group consisting of DNA, RNA, their fragments and their derivatives in which the sample is electrophoresed in an acrylamide gel medium layer provided on a support sheet, the improvement which comprises using as the polyacrylamide gel medium layer for electrophoresis, and aqueous polyacrylamide gel medium layer which is provided on a polymer sheet having been subjected to glow discharge treatment and which contains a water-soluble polymer selected from the group consisting of polyacrylamide and polyethylene glycol, agarose, and a compound selected from the group consisting of urea and formamide, the aqueous polyacrylamide gel medium layer being formed by crosslinking polymerization of an acrylamide compound and a crosslinking agent in the presence of water.

9. The method as claimed in claim 8 in which said water-soluble polymer is contained in an amount of 2 to 100 wt. % based on the polyacrylamide solid amount and said agarose is contained in the aqueous polyacrylamide gel medium in an amount of 0.2 to 2 wt/v %.

10. The method as claimed in claim 8 in which said water-soluble polymer and agarose are dispersed in a three-dimensionally crosslinked polymer formed by the polymerization reaction of the acrylamide compound and the crosslinking agent and are entangled with the three-dimensionally crosslinked polymer structure.

* * * * *